US006692450B1

(12) United States Patent
Coleman (10) Patent No.: US 6,692,450 B1
(45) Date of Patent: Feb. 17, 2004

(54) FOCUSED ULTRASOUND ABLATION DEVICES HAVING SELECTIVELY ACTUATABLE ULTRASOUND EMITTING ELEMENTS AND METHODS OF USING THE SAME

(75) Inventor: R. Glen Coleman, Jacksonville, FL (US)

(73) Assignee: Medtronic Xomed, Inc., Jacksonville, FL (US)

( * ) Notice: Subject to any disclaimer, the term of this patent is extended or adjusted under 35 U.S.C. 154(b) by 0 days.

(21) Appl. No.: 09/487,710

(22) Filed: Jan. 19, 2000

(51) Int. Cl.$^7$ ............................................. A61N 7/02
(52) U.S. Cl. ............................................. 601/3; 601/2
(58) Field of Search ............................ 600/439, 471, 600/472; 601/2, 3, 4

(56) References Cited

U.S. PATENT DOCUMENTS

| 3,990,452 A | 11/1976 | Murry et al. |
| 4,508,122 A | 4/1985 | Gardineer et al. |

(List continued on next page.)

FOREIGN PATENT DOCUMENTS

| WO | WO97/43970 | 11/1997 |

OTHER PUBLICATIONS

Nov. 5, 1998, Company Press Release—FDA Clears First-of-its-Kind Device for Treatment of Sleep Disorder Affecting 20 Million Americans, 4pgs.

May 5, 1998, Clinical Investigations—Radiofrequency Volumetric Tissue Reduction of the Palate in Subjects with Sleep–Disordered Breathing, Nelson B. Powell, MD; Robert W. Riley, DDS, MD; Robert J. Troell, MD; Kasey Li, MD; Marc B. Blumen, MD; Christian Guilleminault, MD, 12 pages.

Jan. 6, 1999, Somnoplasty for Obstructive Sleep Apnea, 1 page.

Jan. 6, 1999, Somnoplasty For the Treatment of Snoring, 2 pgs.

Feb. 17, 1999, Sonablate Technology with HIFU, 2 pages.

(List continued on next page.)

*Primary Examiner*—Marvin M. Lateef
*Assistant Examiner*—Runa Shoh Qaderi (57) ABSTRACT

A focused ultrasound ablation device includes an ultrasound emitting member having a plurality of individual ultrasound emitting elements arranged in an array. The ultrasound emitting elements are selectively, independently actuatable to emit ultrasound energy and focus the emitted ultrasound energy a predetermined distance from the ultrasound emitting member such that the ultrasound energy is focused within anatomical tissue adjacent which the ultrasound emitting member is positioned. The anatomical tissue is heated by the focused ultrasound energy to form a lesion in the tissue of desired size and/or surface configuration. A method of thermal ablation comprises the steps of selecting selected ones of a plurality of ultrasound emitting elements, arranged in an array on an ultrasound emitting member, for actuation to emit ultrasound energy in accordance with a desired size and/or surface configuration of a lesion to be formed in anatomical tissue, positioning the ultrasound emitting member adjacent the tissue, actuating the selected ones of the ultrasound emitting elements to emit ultrasound energy, focusing the ultrasound energy in the tissue with the selected ones of the ultrasound emitting elements, and heating the tissue with the focused ultrasound energy to form a lesion within the tissue having the desired size and/or surface configuration.

42 Claims, 2 Drawing Sheets

U.S. PATENT DOCUMENTS

| | | | |
|---|---|---|---|
| 4,562,900 A | * | 1/1986 | Anderson et al. ............ 181/176 |
| 4,658,828 A | | 4/1987 | Dory |
| 4,807,633 A | | 2/1989 | Fry |
| 4,858,613 A | | 8/1989 | Fry et al. |
| 4,917,096 A | | 4/1990 | Engelhart et al. |
| 4,951,653 A | | 8/1990 | Fry et al. |
| 4,955,365 A | | 9/1990 | Fry et al. |
| RE33,590 E | | 5/1991 | Dory |
| 5,033,456 A | | 7/1991 | Pell et al. |
| 5,036,855 A | | 8/1991 | Fry et al. |
| 5,054,470 A | | 10/1991 | Fry et al. |
| 5,065,761 A | | 11/1991 | Pell |
| 5,080,101 A | | 1/1992 | Dory |
| 5,080,102 A | | 1/1992 | Dory |
| 5,117,832 A | | 6/1992 | Sanghvi et al. |
| 5,134,988 A | | 8/1992 | Pell et al. |
| 5,143,074 A | | 9/1992 | Dory |
| 5,150,711 A | | 9/1992 | Dory |
| 5,150,712 A | | 9/1992 | Dory |
| 5,158,070 A | | 10/1992 | Dory |
| 5,222,501 A | | 6/1993 | Ideker et al. |
| 5,247,935 A | | 9/1993 | Cline et al. |
| 5,267,954 A | | 12/1993 | Nita |
| 5,269,291 A | | 12/1993 | Carter |
| 5,269,297 A | | 12/1993 | Weng et al. |
| 5,295,484 A | | 3/1994 | Marcus et al. |
| 5,304,115 A | | 4/1994 | Pflueger et al. |
| 5,312,328 A | | 5/1994 | Nita et al. |
| 5,318,014 A | | 6/1994 | Carter |
| 5,342,292 A | | 8/1994 | Nita et al. |
| 5,354,258 A | | 10/1994 | Dory |
| 5,380,274 A | | 1/1995 | Nita |
| 5,391,197 A | | 2/1995 | Burdette |
| 5,397,301 A | | 3/1995 | Pflueger et al. |
| 5,409,002 A | | 4/1995 | Pell |
| 5,417,672 A | | 5/1995 | Nita et al. |
| 5,423,812 A | | 6/1995 | Ellman et al. |
| 5,431,621 A | | 7/1995 | Dory |
| 5,431,663 A | | 7/1995 | Carter |
| 5,447,509 A | | 9/1995 | Miller et al. |
| 5,448,994 A | * | 9/1995 | Iinuma ...................... 600/439 |
| 5,456,662 A | | 10/1995 | Edwards et al. |
| 5,474,530 A | | 12/1995 | Passafaro et al. |
| 5,492,126 A | | 2/1996 | Hennige et al. |
| 5,501,655 A | | 3/1996 | Rolt et al. |
| 5,514,131 A | | 5/1996 | Edwards |
| 5,520,188 A | | 5/1996 | Hennige et al. |
| 5,542,917 A | | 8/1996 | Nita et al. |
| 5,620,479 A | | 4/1997 | Diederich |
| 5,624,439 A | | 4/1997 | Edwards |
| 5,674,191 A | | 10/1997 | Edwards |
| 5,676,692 A | | 10/1997 | Sanghvi et al. |
| 5,707,349 A | | 1/1998 | Edwards |
| 5,718,702 A | | 2/1998 | Edwards |
| 5,720,719 A | | 2/1998 | Edwards et al. |
| 5,728,094 A | | 3/1998 | Edwards |
| 5,730,719 A | | 3/1998 | Edwards |
| 5,733,315 A | | 3/1998 | Burdette et al. |
| 5,735,280 A | | 4/1998 | Sherman et al. |
| 5,738,114 A | | 4/1998 | Edwards |
| 5,743,870 A | | 4/1998 | Edwards |
| 5,743,904 A | | 4/1998 | Edwards |
| 5,746,224 A | | 5/1998 | Edwards |
| 5,762,066 A | | 6/1998 | Law et al. |
| 5,800,379 A | | 9/1998 | Edwards |
| 5,800,429 A | | 9/1998 | Edwards |
| 5,800,482 A | | 9/1998 | Pomeranz et al. |
| 5,807,308 A | | 9/1998 | Edwards |
| 5,817,049 A | | 10/1998 | Edwards |
| 5,823,197 A | | 10/1998 | Edwards |
| 5,827,277 A | | 10/1998 | Edwards |
| 5,843,077 A | | 12/1998 | Edwards |
| 5,871,524 A | | 2/1999 | Knowlton |
| 5,873,845 A | | 2/1999 | Cline et al. |
| 5,873,902 A | | 2/1999 | Sanghvi et al. |
| 5,879,349 A | | 3/1999 | Edwards |
| 5,882,302 A | | 3/1999 | Driscoll, Jr. et al. |
| 5,895,356 A | | 4/1999 | Andrus et al. |
| 5,928,169 A | | 7/1999 | Schätzle et al. |
| 5,938,608 A | | 8/1999 | Bieger et al. |
| 5,984,881 A | | 11/1999 | Ishibashi et al. |
| 5,984,882 A | | 11/1999 | Rosenschein et al. |
| 6,007,499 A | | 12/1999 | Martin et al. |
| 6,026,816 A | | 2/2000 | McMillan et al. |
| 6,096,033 A | | 8/2000 | Tu et al. |
| 6,113,559 A | | 9/2000 | Klopotek |
| 6,126,619 A | * | 10/2000 | Peterson et al. ................ 601/2 |
| 6,126,657 A | | 10/2000 | Edwards et al. |
| 6,135,971 A | | 10/2000 | Hutchinson et al. |
| 6,174,280 B1 | | 1/2001 | Oneda et al. |
| 6,190,381 B1 | | 2/2001 | Olsen et al. |
| 6,210,355 B1 | | 4/2001 | Edwards et al. |
| 6,217,530 B1 | | 4/2001 | Martin et al. |
| 6,241,753 B1 | | 6/2001 | Knowlton |
| 6,309,355 B1 | | 10/2001 | Cain et al. |
| 6,325,769 B1 | | 12/2001 | Klopotek |

OTHER PUBLICATIONS

Feb. 23, 1999, Focus Surgery, (McDonald & Company), 1 page.

May 5, 1997, Laboratory and animal investigations—Radiofrequency Volumetric Reduction of the Tongue, Nelson B. Powell, MD; Robert W. Riley, MD; Robert J. Troell, MD; Marc B. Blumen, MD; Christian Guilleminault, MD, 8 pages.

* cited by examiner

FOCUSED ULTRASOUND ABLATION DEVICES HAVING SELECTIVELY ACTUATABLE ULTRASOUND EMITTING ELEMENTS AND METHODS OF USING THE SAME

CROSS-REFERENCE TO RELATED PATENT APPLICATIONS

This application is related to U.S. patent applications entitled Methods of Soft Palate Reduction By Thermal Ablation Using High Intensity Focused Ultrasound, Methods of Tongue Reduction By Thermal Ablation Using High Intensity Focused Ultrasound, Methods of Tonsil Reduction By Thermal Ablation Using High Intensity Focused Ultrasound, Methods of Turbinate Or Other Soft Tissue Reduction By Thermal Ablation Using High Intensity Focused Ultrasound, Methods of Skin Rejuvenation By Thermal Stimulation Using High Intensity Focused Ultrasound, and Focused Ultrasound Ablation Devices Having Malleable Handle Shafts and Methods of Using the Same, the disclosures of which are incorporated herein by reference

BACKGROUND OF THE INVENTION

1. Field of the Invention

The present invention relates generally to the treatment of anatomical tissue with high intensity focused ultrasound energy and, more particularly, to focused ultrasound ablation devices by which lesions of selected sizes and/or configurations are formed in anatomical tissue and to methods of thermal ablation using the same.

2. Brief Description of the Related Art

When high intensity ultrasound energy is applied to anatomical tissue, significant physiological effects may be produced in the anatomical tissue resulting from thermal and/or mechanical changes or effects in the tissue. Thermal effects include heating of the anatomical tissue; and, when the tissue is heated to a sufficiently high temperature, tissue damage such as coagulative necrosis is produced. In order to produce thermal effects in anatomical tissue, ultrasound emitting members such as transducers have been used to emit ultrasound energy which is applied to anatomical tissue by positioning the ultrasound emitting members adjacent or in contact with the tissue or by coupling the ultrasound emitting members to the tissue via an acoustic coupling medium. By focusing the ultrasound energy at one or more specific focusing zones within the tissue, thermal effects can be confined to a defined location, region, volume or area, and such location, region, volume or area can be remote from the ultrasound emitting member.

With the use of high intensity focused ultrasound (HIFU), one or more focusing zones at or within a designated target location, region, volume or area within a larger mass, body or area of anatomical tissue can be subjected to high intensity ultrasound energy while tissue surrounding the target area is subjected to much lower intensity ultrasound energy. In this manner, tissue at the target area can be heated to a sufficiently high temperature so as to cause a desired thermal effect such as tissue damage, ablation, coagulation, denaturation, destruction or necrosis while tissue surrounding the target area is not heated to damaging temperatures and, therefore, is preserved. Heating of tissue at a target location, volume, region or area to an ablative temperature creates an ablative lesion in the tissue at the target location, volume, region or area that is desirable in the treatment of various medical conditions, disorders or diseases. For example, the lesion may remain as tissue having altered characteristics or may be naturally degraded and absorbed by the patient's body and thusly eliminated such that the remaining body, mass or area of tissue is of smaller volume or size due to the absence of the ablated tissue.

The use of high intensity focused ultrasound to eliminate tissue or to alter the characteristics of tissue at a target location, volume, region or area within a larger mass, body or area of anatomical tissue presents many advantages including minimization of trauma and pain for the patient, elimination of the need for a surgical incision, stitches and exposure of internal tissue, avoidance of damage to tissue other than that which is to be treated, altered or removed, lack of a harmful cumulative effect from the ultrasound energy on the surrounding non-target tissue, reduction in treatment costs, elimination of the need in many cases for general anesthesia, reduction of the risk of infection and other complications, avoidance of blood loss, and the ability for high intensity focused ultrasound procedures to be performed in non-hospital sites and/or on an out-patient basis.

Various ultrasound treatment devices and/or methods for treating anatomical tissue with ultrasound have been proposed as represented by U.S. Pat. No. Re. 33,590 to Dory, U.S. Pat. No. 3,990,452 to Murry et al, U.S. Pat. No. 4,658,828 to Dory, U.S. Pat. No. 4,807,633 to Fry, U.S. Pat. No. 4,858,613 to Fry et al, U.S. Pat. No. 4,951,653 to Fry et al, U.S. Pat. No. 4,955,365 to Fry et al, U.S. Pat. No. 5,033,456 to Pell et al, U.S. Pat. No. 5,036,855 to Fry et al, U.S. Pat. No. 5,054,470 to Fry et al, U.S. Pat. No. 5,065,761 to Pell, U.S. Pat. No. 5,080,101 to Dory, U.S. Pat. No. 5,080,102 to Dory, U.S. Pat. No. 5,117,832 to Sanghvi et al, U.S. Pat. No. 5,134,988 to Pell et al, U.S. Pat. No. 5,143,074 to Dory, U.S. Pat. No. 5,150,711 to Dory, U.S. Pat. No. 5,150,712 to Dory, U.S. Pat. No. 5,158,070 to Dory, U.S. Pat. No. 5,222,501 to Ideker et al, U.S. Pat. No. 5,267,954 to Nita, U.S. Pat. No. 5,269,291 to Carter, U.S. Pat. No. 5,269,297 to Weng et al, U.S. Pat. No. 5,295,484 to Marcus et al, U.S. Pat. No. 5,304,115 to Pflueger et al, U.S. Pat. No. 5,312,328 to Nita et al, U.S. Pat. No. 5,318,014 to Carter, U.S. Pat. No. 5,342,292 to Nita et al, U.S. Pat. No. 5,354,258 to Dory, U.S. Pat. No. 5,380,274 to Nita, U.S. Pat. No. 5,391,197 to Burdette et al, U.S. Pat. No. 5,397,301 to Pflueger et al, U.S. Pat. No. 5,409,002 to Pell, U.S. Pat. No. 5,417,672 to Nita et al, U.S. Pat. No. 5,431,621 to Dory, U.S. Pat. No. 5,431,663 to Carter, U.S. Pat. No. 5,447,509 to Mills et al, U.S. Pat. No. 5,474,530 to Passafaro et al, U.S. Pat. No. 5,492,126 to Hennige et al, U.S. Pat. No. 5,501,655 to Rolt et al, U.S. Pat. No. 5,520,188 to Hennige et al, U.S. Pat. No. 5,542,917 to Nita et al, U.S. Pat. No. 5,620,479 to Diederich, U.S. Pat. No. 5,676,692 to Sanghvi et al, U.S. Pat. No. 5,728,094 to Edwards, U.S. Pat. No. 5,730,719 to Edwards, U.S. Pat. No. 5,733,315 to Burdette et al, U.S. Pat. No. 5,735,280 to Sherman et al, U.S. Pat. No. 5,738,114 to Edwards, U.S. Pat. No. 5,746,224 to Edwards, U.S. Pat. No. 5,762,066 to Law et al, U.S. Pat. No. 5,800,379 to Edwards, U.S. Pat. No. 5,800,429 to Edwards, U.S. Pat. No. 5,800,482 to Pomeranz et al, U.S. Pat. No. 5,807,308 to Edwards, U.S. Pat. No. 5,817,049 to Edwards, U.S. Pat. No. 5,823,197 to Edwards, U.S. Pat. No. 5,827,277 to Edwards, U.S. Pat. No. 5,843,077 to Edwards, U.S. Pat. No. 5,871,524 to Knowlton, U.S. Pat. No. 5,873,845 to Cline et al, U.S. Pat. No. 5,873,902 to Sanghvi et al, U.S. Pat. No. 5,879,349 to Edwards, U.S. Pat. No. 5,882,302 to Driscoll, Jr. et al, U.S. Pat. No. 5,895,356 to Andrus et al, U.S. Pat. No. 5,928,169 to Schätzle and U.S. Pat. No. 5,938,608 to Bieger et al.

In particular, focused ultrasound ablation devices used to thermally damage, ablate, coagulate, denature, cauterize, necrotize or destroy a target volume of tissue are exemplified by U.S. Pat. No. Re. 33,590 to Dory, U.S. Pat. No. 4,658,828 to Dory, U.S. Pat. No. 4,807,633 to Fry, U.S. Pat. No. 4,858,613 to Fry et al, U.S. Pat. No. 4,951,653 to Fry et al, U.S. Pat. No. 4,955,365 to Fry et al, U.S. Pat. No. 5,036,855 to Fry et al, U.S. Pat. No. 5,054,470 to Fry et al, U.S. Pat. No. 5,080,101 to Dory, U.S. Pat. No. 5,080,102 to Dory, U.S. Pat. No. 5,117,832 to Sanghvi et al, U.S. Pat. No. 5,143,074 to Dory, U.S. Pat. No. 5,150,711 to Dory, U.S. Pat. No. 5,150,712 to Dory, U.S. Pat. No. 5,295,484 to Marcus et al, U.S. Pat. No. 5,354,258 to Dory, U.S. Pat. No. 5,391,197 to Burdette et al, U.S. Pat. No. 5,431,621 to Dory, U.S. Pat. No. 5,492,126 to Hennige et al, U.S. Pat. No. 5,501,655 to Rolt et al, U.S. Pat. No. 5,520,188 to Hennige et al, U.S. Pat. No. 5,676,692 to Sanghvi et al, U.S. Pat. No. 5,733,315 to Burdette et al, U.S. Pat. No. 5,762,066 to Law et al, U.S. Pat. No. 5,871,524 to Knowlton, U.S. Pat. No. 5,873,845 to Cline et al, U.S. Pat. No. 5,873,902 to Sanghvi et al, U.S. Pat. No. 5,882,302 to Driscoll, Jr. et al, U.S. Pat. No. 5,895,356 to Andrus et al, U.S. Pat. No. 5,928,169 to Schätzle et al and U.S. Pat. No. 5,938,608 to Bieger et al. The focused ultrasound ablation devices are used to ablate various target areas in or on the bodies of patients including the brain, prostate, heart, urethra, blood vessels, deep seated tissue and tumors, liver, kidney, skin, breast, stomach and pancreas.

Ablation of anatomical tissue of the head and/or neck in order to treat various airway related disorders has also been proposed as illustrated by U.S. Pat. No. 5,423,812 to Ellman et al, U.S. Pat. Nos. 5,456,662, 5,514,131, 5,624,439, 5,674,191, 5,707,349, 5,718,702, 5,728,094, 5,730,719, 5,738,114, 5,743,870, 5,743,904, 5,746,224, 5,800,379, 5,800,429, 5,807,308, 5,817,049, 5,823,197, 5,827,277, 5,843,077 and 5,879,349 to Edwards and WO 97/43970. The areas ablated include the soft palate, uvula, tongue, tonsils, adenoids and turbinates. U.S. Pat. No. 5,423,812 relates to electrosurgical stripping of tissue. U.S. Pat. No. 5,456,662, U.S. Pat. No. 5,514,131, U.S. Pat. No. 5,624,439, U.S. Pat. No. 5,674,191, U.S. Pat. No. 5,707,349, U.S. Pat. No. 5,718,702, U.S. Pat. No. 5,728,094, U.S. Pat. No. 5,730,719, U.S. Pat. No. 5,738,114, U.S. Pat. No. 5,743,870, U.S. Pat. No. 5,743,904, U.S. Pat. No. 5,746,224, U.S. Pat. No. 5,800,379, U.S. Pat. No. 5,800,429, U.S. Pat. No. 5,807,308, U.S. Pat. No. 5,817,049, U.S. Pat. No. 5,823,197, U.S. Pat. No. 5,827,277, U.S. Pat. No. 5,843,077, U.S. Pat. No. 5,879,349 and WO97/43970 disclose RF ablation using tissue penetrating electrodes. U.S. Pat. No. 5,707,349, U.S. Pat. No. 5,728,094, U.S. Pat. No. 5,730,719, U.S. Pat. No. 5,738,114, U.S. Pat. No. 5,746,224, U.S. Pat. No. 5,800,379, U.S. Pat. No. 5,800,429, U.S. Pat. No. 5,807,308, U.S. Pat. No. 5,817,049, U.S. Pat. No. 5,823,197, U.S. Pat. No. 5,827,277, U.S. Pat. No. 5,843,077 and U.S. Pat. No. 5,879,349 refer to ultrasound as a possible source of ablative energy.

Prior focused ultrasound ablation devices typically have ultrasound emitting members, commonly including transducers, for emitting ultrasound energy and focusing the ultrasound energy at target areas in anatomical tissue in order to effect thermal ablation at the target areas. Exemplary focused ultrasound ablation devices employing transducers as the ultrasound emitting members thereof are disclosed in U.S. Pat. No. 4,658,828 to Dory, U.S. Pat. Nos. 4,858,613, 4,951,653, 4,955,365, 5,036,855 and 5,054,470 to Fry et al, U.S. Pat. Nos. 5,080,101 and 5,080,102 to Dory, U.S. Pat. No. 5,117,832 to Sanghvi et al, U.S. Pat. Nos. 5,143,074, 5,150,711 and 5,150,712 to Dory, U.S. Pat. No. 5,295484 to Marcus et al, U.S. Pat. No. 5,354,258 to Dory, U.S. Pat. No. 5,391,197 to Burdette et al, U.S. Pat. No. 5,431,621 to Dory, U.S. Pat. No. 5,492,126 to Hennige et al, U.S. Pat. No. 5,501,655 to Rolt et al, U.S. Pat. No. 5,520,188 to Hennige et al, U.S. Pat. No. 5,676,692 to Sanghvi et al, U.S. Pat. No. 5,762,066 to Law et al, U.S. Pat. No. 5,873,845 to Cline et al, U.S. Pat. No. 5,873,902 to Sanghvi et al, U.S. Pat. No. 5,882,302 to Driscoll, Jr. et al, U.S. Pat. No. 5,895,356 to Andrus et al, U.S. Pat. No. 5,928,169 to Schätzle et al, U.S. Pat. No. 5,938,608 to Bieger et al and U.S. Pat. No. Re. 33,590 to Dory.

Some prior focused ultrasound ablation devices employ arrays or pluralities of transducer elements as the ultrasound emitting members, respectively, as represented by U.S. Pat. Nos. 4,658,828, 5,080,101, 5,080,102, 5,143,074, 5,150,712 and U.S. Pat. No. Re. 33,590 to Dory, U.S. Pat. No. 5,391,197 to Burdette et al, U.S. Pat. No. 5,501,655 to Rolt et al, U.S. Pat. No. 5,520,188 to Hennige et al, U.S. Pat. No. 5,928,169 to Schätzle et al and U.S. Pat. No. 5,938,608 to Bieger et al. U.S. Pat. Nos. 4,658,828, 5,080,101, 5,080,102, 5,150,712, 5,501,655, 5,520,188, 5,928,169, 5,938,608 and U.S. Pat. No. Re. 33,590 disclose the transducer elements as being actuated or driven in phase-offset relation to one another in order to change the location at which the ultrasound energy is focused in anatomical tissue.

U.S. Pat. Nos. 5,746,224 and 5,800,429 to Edwards disclose an energy delivery device comprising one or more ring electrodes to which RF energy may be independently delivered to effect thermal ablation of tissue. Ultrasound is merely referred to as a possible source of ablative energy.

In order to enhance the efficacy of focused ultrasound ablation procedures, it would be desirable to customize or tailor lesions to be formed in particular patients for particular procedures. For example, it would be desirable for a single focused ultrasound ablation device to be capable of forming lesions of various sizes and/or configurations or patterns in anatomical tissue including lesions of various irregular or discontinuous patterns. Also, it would be desirable for a focused ultrasound ablation device to be capable of forming a lesion comprising disconnected lesion segments. By providing a focused ultrasound ablation device having the foregoing attributes, optimum lesion characteristics can be selected for particular patients and procedures based on assessments made by surgeons or other medical personnel at the time of surgery. However, prior focused ultrasound ablation devices, as exemplified by the above-mentioned patents, do not provide focused ultrasound emitting members having the foregoing attributes.

SUMMARY OF THE INVENTION

Accordingly, it is a primary object of the present invention to overcome the various disadvantages of prior focused ultrasound ablation devices.

It is also an object of the present invention to provide a focused ultrasound ablation device having an ultrasound emitting member capable of forming lesions of various preselected configurations in anatomical tissue.

Another object of the present invention is to provide a focused ultrasound ablation device having an ultrasound emitting member capable of forming a lesion comprising a plurality of disconnected lesion segments in anatomical tissue.

A further object of the present invention is to selectively actuate less than all of a plurality of ultrasound emitting elements of a focused ultrasound emitting member in order to form a lesion of selected size and/or configuration in anatomical tissue.

An additional object of the present invention is to increase the diversity of sizes and/or configurations of lesions capable of being formed in anatomical tissue using focused ultrasound ablation devices.

It is also an object of the present invention to electronically control the actuation of selected ones of a plurality of ultrasound emitting elements of a focused ultrasound emitting member to form a lesion of optimal size and/or configuration in anatomical tissue of a patient.

The present invention also has as an object to provide a multi-array transducer including a plurality of transducer elements that are selectively actuatable to form lesions of various preselected sizes and/or configurations in patients.

Some of the advantages of the present invention are that the outcome of ultrasound ablation procedures in various areas of the body is greatly enhanced, a single focused ultrasound ablation device can optimally be used in various ablation procedures in various areas of the body, anatomical tissue around, between or surrounding the lesion segments can be left undamaged and lesion free, a focused ultrasound emitting member having a particular array of transducer elements can be used to form lesions corresponding in size and/or configuration to the overall size and/or configuration of the array as well as lesions having sizes and/or configurations different from the overall size and/or configuration of the array, the focused ultrasound emitting member can be coupled with a handle for hand-held use and operation thereof, the focused ultrasound ablation device does not have to be customized for use in a specific area of the body, and the focused ultrasound emitting member can be provided in a focused ultrasound ablation device provided as a standardized instrument capable of being used in or on a wide variety of areas of patients' bodies.

These and other objects, advantages and benefits are realized with the present invention as generally characterized in a focused ultrasound ablation device including an ultrasound emitting member having a plurality of individual ultrasound emitting elements arranged in an array. The ultrasound emitting elements are actuatable to emit ultrasound energy and focus the emitted ultrasound energy at focusing zones, respectively, located a predetermined distance from the ultrasound emitting member. The focusing zones are within a target area in anatomical tissue adjacent which the ultrasound emitting member is placed. The focused ultrasound energy causes the anatomical tissue at the target area to be heated to an ablative temperature to form a lesion. The ultrasound emitting elements are selectively, independently actuatable, allowing selected ones of the ultrasound emitting elements to be actuated to emit ultrasound energy to obtain a lesion of desired or selected size and/or surface configuration. The lesion size and/or surface configuration corresponds to the locations of and/or pattern formed by the ultrasound emitting elements selected for actuation. In this manner, lesion characteristics can be optimally selected for particular patients and particular ablation procedures to be performed. In a preferred embodiment, the ultrasound emitting elements are transducer elements including piezoelectric elements that emit ultrasound energy in response to an electric signal supplied thereto, and selected ones of the transducer elements are selected for actuation by selectively coupling the selected elements to the electrical signal.

A method of thermal ablation of anatomical tissue according to the present invention is generally characterized by the steps of selecting selected ones of a plurality of ultrasound emitting elements, arranged in an array on an ultrasound emitting member, for actuation to emit ultrasound energy in accordance with a desired size and/or configuration of a lesion to be formed in anatomical tissue of a patient, positioning the ultrasound emitting member adjacent or in contact with the anatomical tissue at a location aligned with a target area in the tissue, actuating the selected ones of the ultrasound emitting elements to emit ultrasound energy, focusing the ultrasound energy emitted by the selected ones of the ultrasound emitting elements at focusing zones, respectively, within the target area and heating the tissue of the target area with the focused ultrasound energy to form a lesion having the desired size and/or configuration.

Other objects and advantages of the present invention will become apparent from the following description of the preferred embodiments taken in conjunction with the accompanying drawings, wherein marked parts in each of the several figures are identified by the same reference characters.

DESCRIPTION OF THE PREFERRED EMBODIMENTS

Figures 1, 2, 3, 4, 5:
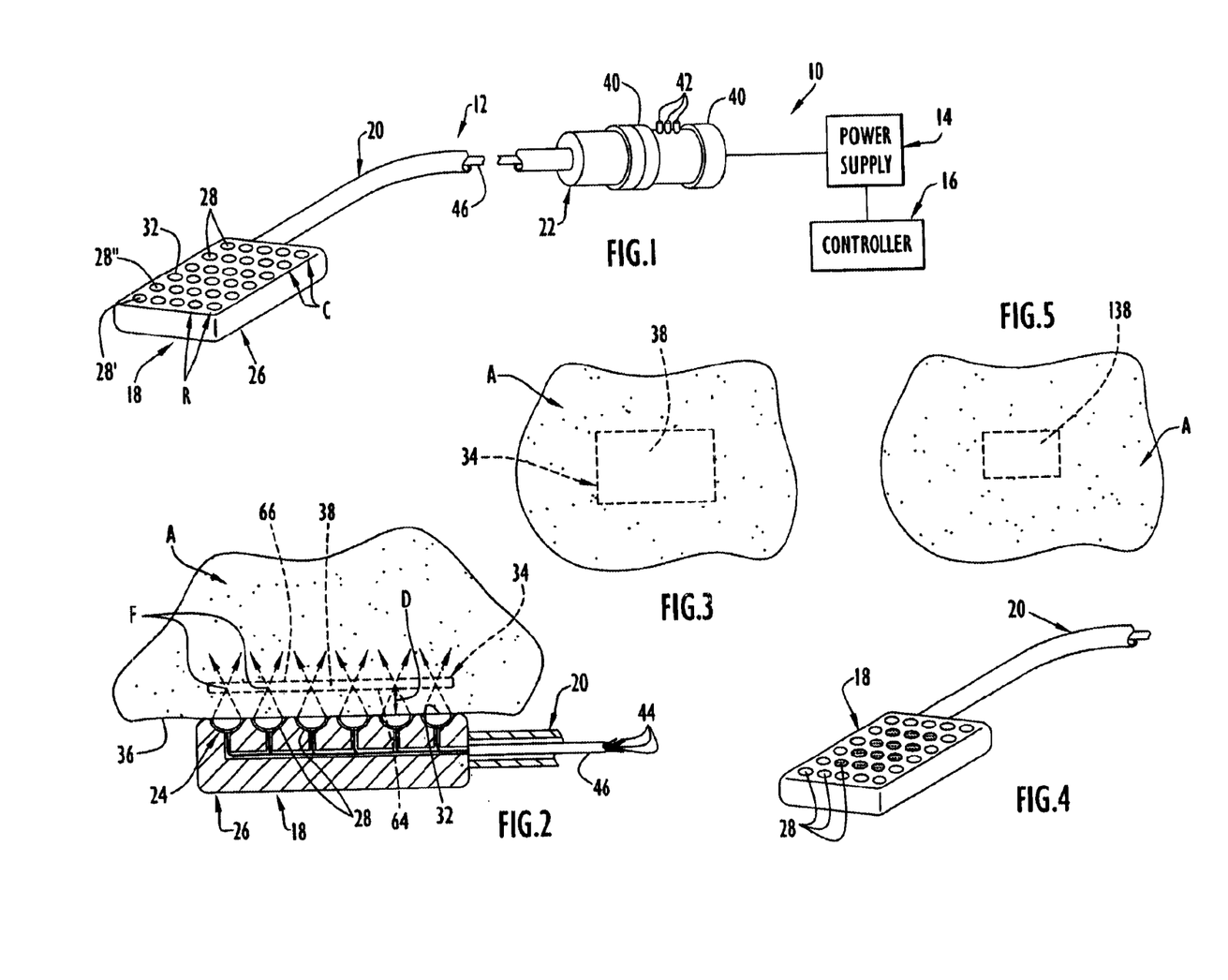
FIG. 1 is a broken perspective view, partly schematic, illustrating a focused ultrasound ablation assembly incorporating a focused ultrasound ablation device according to the present invention.
FIG. 2 is a broken side view, partly in section, of an ultrasound emitting member of the focused ultrasound ablation device depicting actuation of all of a plurality of ultrasound emitting elements of the ultrasound emitting member to emit ultrasound energy and focus the ultrasound energy in anatomical tissue to form a lesion.
FIG. 3 is a broken top view illustrating the surface configuration of the lesion of FIG. 2.
FIG. 4 is a broken perspective view of the ultrasound emitting member illustrating actuation of selected ones of the plurality of ultrasound emitting elements, such selected ones of the plurality of ultrasound emitting elements consisting of less than all of the ultrasound emitting elements.
FIG. 5 is a broken top view illustrating the surface configuration of a lesion formed in tissue with the focused ultrasound emitting member when actuated as shown in FIG. 4.

A focused ultrasound ablation assembly or system 10 incorporating a focused ultrasound ablation device 12 according to the present invention is illustrated in FIG. 1. The focused ultrasound ablation assembly 10 includes focused ultrasound ablation device 12, a power supply 14 and a controller 16. The focused ultrasound ablation device 12 includes a focused ultrasound emitting member 18, an elongate handle shaft or handle body 20 having a distal end at which the ultrasound emitting member is disposed and a handle or handpiece 22 coupled to a proximal end of handle shaft 20. As shown in FIG. 2, the ultrasound emitting member includes a transducer 24 carried by or within a housing, carrier or case 26 and capable of generating and emitting ultrasound energy in response to being supplied with electrical power from power supply 14. The transducer 24 includes a plurality of individual ultrasound emitting elements or transducer elements 28, each including a piezoelectric element that vibrates to produce ultrasound energy when electrical current or signal is supplied thereto. The transducer elements 28 have a focusing configuration or geometry that results in the ultrasound energy produced thereby being focused a fixed distance from the ultrasound emitting member. The transducer elements 28 have a partial spherical or concave configuration causing the ultrasound energy generated thereby to be focused, as shown by arrows in FIG. 2, at focusing zones F, respectively.

The transducer elements 28 are arranged in an array on or in housing 26; and, therefore, the transducer 24 may be considered a multi-array transducer. In the case of ultrasound emitting member 18, the transducer elements are arranged in a planar array of five rows R and six columns C, although the transducer elements can be arranged in any number of rows and columns depending on the number of transducer elements provided in the ultrasound emitting member. In the case of focused ultrasound emitting member 18, each row R has an equal number of transducer elements, and each column C has an equal number of transducer elements. It should be appreciated that any number of transducer elements can be provided in each row and column and that the numbers of transducer elements provided in each row and column can be the same or different.

The transducer elements 28 can be referenced by their location in the array. For example, the transducer element 28' in the first row, first column can be designated transducer element R1C1, the transducer element 28" in the first row, second column can be designated transducer element R1C2 and so on. The transducer elements of each row are disposed close to one another, and the transducer elements of each column are disposed close to one another such that there is minimal space between adjacent transducer elements. As explained further below, the transducer elements 28 are selectively, independently actuatable to selectively emit or not emit ultrasound energy.

The transducer elements 28 can be designed in various ways as known in the art. In the case of transducer 24, the transducer elements each comprise a piezoelectric element formed by a layer of piezoelectric material carried by housing 26. The piezoelectric elements are recessed from a planar external top surface 32 of housing 26. The piezoelectric elements are curved in a direction inwardly of surface 32 such that ultrasound energy generated by the piezoelectric elements is emitted from focused ultrasound emitting member 18 in a direction perpendicular or normal to surface 32 for focusing at the focusing zones F, which are spaced outwardly of surface 32. Accordingly, surface 32 is an active surface or face of the ultrasound emitting member which, when positioned externally adjacent or in contact with a mass, body or area of anatomical tissue A, results in the ultrasound energy emitted by the transducer being focused at zones F, which will be disposed within the anatomical tissue A as shown in FIG. 2. When the ultrasound emitting member is positioned on, against or adjacent the tissue A at a location aligned with a designated target area 34 within the tissue A, the focusing zones will be disposed at or within the target area as shown in FIG. 2.

Each focusing zone F consists of a single point or a plurality of points forming a zone at which the ultrasound energy is focused. Each focusing zone F is in line with a central axis of the corresponding transducer element. Each focusing zone is disposed a fixed predetermined distance D from a plane containing active face 32, the distance D for each focusing zone being perpendicular or normal to the active face. Therefore, the focusing zones F will also be disposed a predetermined perpendicular distance or a calculable or determinable perpendicular distance from an external tissue surface 36 of tissue A with which the active face 32 is placed in contact or adjacent thereto. Where the active face 32 is placed in contact with the external tissue surface 36, the perpendicular distance that zones F are disposed from external tissue surface 36 will be the same as the predetermined distance D as shown in FIG. 2. Where the active face 32 is not placed in contact with the external tissue surface 36 but, rather, is spaced from the external tissue surface 36 by a known amount, for example, the perpendicular distance that zones F are disposed from the external tissue surface will correspond to distance D minus the distance that the active face is spaced from the external tissue surface. Where the active face 32 is spaced from the external tissue surface 36, an acoustic coupling medium can be disposed between the external tissue surface 36 and the member 18 as disclosed in the patent applications incorporated herein by reference and entitled Methods of Soft Palate Reduction By Thermal Ablation Using High Intensity Focused Ultrasound, Methods of Tongue Reduction By Thermal Ablation Using High Intensity Focused Ultrasound, Methods of Tonsil Reduction By Thermal Ablation Using High Intensity Focused Ultrasound, Methods of Turbinate Or Other Soft Tissue Reduction By Thermal Ablation Using High Intensity Focused Ultrasound, Methods of Skin Rejuvenation By Thermal Stimulation Using High Intensity Focused Ultrasound and Focused Ultrasound Ablation Devices Having Malleable Handle Shafts and Methods of Using the Same.

Since the ultrasound is focused at zones F, the ultrasound is of greater or higher intensity at focusing zones F and is thusly focused or concentrated at the focusing zones F, causing tissue A at the focusing zones F to be heated to an ablative temperature. When all of the transducer elements 28 are actuated, as shown in FIG. 2, heating of tissue A will occur at a focusing zone F for each transducer element. Since the transducer elements are disposed close to one another, the areas of tissue between the focusing zones are also heated to an ablative temperature due to thermal conduction causing the dispersal or spread of heat from the focusing zones. Accordingly, a discrete, definitive lesion 38 is formed in the tissue while the temperature of the tissue surrounding the lesion remains below damaging levels such that the surrounding tissue is undamaged and preserved. When all of the transducer elements 28 are actuated, a lesion of specific configuration and size is created within the body, mass or area of anatomical tissue A for the transducer 24 in accordance with the intensity level of the emitted ultrasound energy and the duration or time of ultrasound energy delivery to the tissue. Accordingly, a lesion having a specific length, width and depth is formed in the tissue. FIGS. 2 and 3 illustrate the lesion 38 formed in tissue A when all of the transducer elements are actuated. The lesion 38 has a generally rectangular configuration with a predetermined length and width dictated by the configuration of the array and a predetermined depth dictated by the length of the focusing zones. When the ultrasound emitting member 18 is positioned on, against or adjacent the tissue A at a location aligned with a designated target or lesion area 34 in the tissue, the lesion 38 will be formed at or coincide with the target area as shown in FIGS. 2 and 3.

The housing 26 can have various external configurations and sizes in accordance with the size, configuration and design of the transducer and the array in which the transducer elements are arranged including rectangular, square, circular, curved and cylindrical or tubular configurations. In the case of ultrasound emitting member 18, the housing 26 has a generally rectangular external configuration with rounded or blunt corners and/or edges to avoid damage to anatomical tissue. It should be appreciated that the transducer elements 28 can be disposed within the housing with the ultrasound energy generated by transducer elements being transmitted or emitted through or from a wall of the housing, such wall being made of material through which ultrasound energy can pass and defining the active face for the ultrasound emitting member. Of course, a surface of the transducer itself can define the active face for the ultrasound emitting member.

The active face for ultrasound emitting member 18 is parallel to a longitudinal axis of member 18 so that the predetermined distance for zones F beyond the active face and the external tissue surface is perpendicular to the longitudinal axis. It should be appreciated that, depending on the design of the ultrasound emitting member, the predetermined distances for the focusing zones beyond the active face and the external tissue surface can be perpendicular to the active face but non-perpendicular to the longitudinal axis. The active face may be rigid or flexible or deformable depending on procedural use. The active face and/or the transducer may be designed to conform to the shape of the tissue surface against which the active face is placed. Of course, where soft tissue is being ablated, the soft tissue may conform to the shape of the active face and/or the transducer where the active face and/or the transducer is/are more rigid than the tissue.

The handle shaft 20 comprises an elongate, hollow or tubular member of sufficient length to position the ultrasound emitting member 18 at various operative sites in or on the body of a patient while the handle 22 is maintained at a remote location, typically externally of the patient's body. Preferably, the handle shaft 20 is malleable as disclosed in the application entitled Focused Ultrasound Ablation Devices Having Malleable Handle Shafts and Methods of Using the Same, the disclosure of which is incorporated herein by reference. The distal end of handle shaft 20 is coupled with the ultrasound emitting member by being disposed on or within an end wall of housing 26 or by extending through the end wall of housing 26 to be disposed within the housing.

The handle 22 has a forward end coupled to the proximal end of handle shaft 20 and has a rearward end. The handle 22 preferably has a configuration to facilitate grasping by a surgeon or other operator. In the case of focused ultrasound ablation device 12, the handle 22 has a cylindrical body with raised, external annular segments 40. The segments 40 are longitudinally spaced from one another, and one or more controls or switches 42, such as push button controls or switches, may be disposed on handle 22 between spaced segments 40. The one or more controls or switches 42, where provided, may be used to effect operation of the focused ultrasound ablation device. It should be appreciated that the handle can be provided without controls or switches in which case operation of the focused ultrasound ablation device may be effected by one or more controls or switches located on the power supply, the controller and/or a dedicated structure such as a foot pedal. Where the one or more controls or switches are provided on the handle 22, as illustrated for focused ultrasound ablation device 12, the one or more controls or switches is/are desirably placed at a location on the handle amenable to convenient operation thereof by the hand of the surgeon or other operator grasping the handle. As shown in FIG. 1, the push button controls or switches 42 are accessible and operable by a finger of a hand grasping -the handle 22 for one-handed operation of ablation device 12.

The proximal end of handle shaft 20 is coupled with handle 22 at the forward end thereof and, in particular, at a forward wall of the handle. The proximal end of handle shaft 20 may be disposed on or within the forward wall or may extend through the forward wall to be disposed within the handle 22. With the proximal end of the handle shaft thusly coupled to the handle, the longitudinal axis of handle is coaxially aligned with the longitudinal axis of the handle shaft at the proximal end thereof. The shaft and the handle are preferably made of a material or materials that does/do not transmit ultrasound energy to the surgeon or other operator.

One or more electrical transmission wires 44 is/are connected to the transducer 24 and extend through the handle shaft 20 for connection with power supply 14 in order to transmit or supply electric current from the power supply to the transducer. The power supply may be disposed partly or entirely in the handle, or may be provided separately as a console or unit coupled to the handle shaft or the handle via one or more appropriate transmission wires, which may be the same or different from the one or more transmission wires 44. For example, an electrical cord of suitable length may be removably coupled between the handle 22 and the power supply 14. The power supply 14 can be designed in various ways as a source or supply of electricity to activate or excite transducer 24 to generate and emit ultrasound energy. For example, the power supply can be designed to provide high frequency alternating electrical current to the transducer via the one or more transmission wires. The power supply may include an RF generator, with or without an amplifier, providing a constant current source. Electrical current provided by the power supply is selectively discharged into all or selected ones of the piezoelectric elements, producing vibration of all or selected ones of the piezoelectric elements and, therefore, producing acoustic or ultrasonic waves or energy. The power supply may be separate from the handle but may be operated via controls 42 on the handle.

In the case of focused ultrasound ablation device 12, a transmission wire 44 is provided for each piezoelectric element and, therefore, for each transducer element. As shown in FIG. 2, each transmission wire 44 is connected to its corresponding piezoelectric element and to the power supply so that the transducer elements are individually driven by or supplied with current from the power supply. The transmission wires 44 are disposed in respective passages within the housing and may be disposed within a sheath or sleeve 46 extending through shaft 20. The transmission wires 44 are connected to switches (not shown), respectively, for controlling the supply or transmission of current from the power supply 16 to the piezoelectric elements, respectively. The switches can be incorporated in the ultrasound emitting member 18, the power supply 14 and/or the controller 16.

The controller or control unit 16 controls the supply of power from power supply 14 to transducer 24 so that the transducer can be driven to deliver various intensity levels of ultrasound energy for various durations, periods or lengths of time. In particular, the controller 16 controls the supply of the power from power supply to the individual piezoelectric elements so that the transducer elements can be individually driven or actuated to emit ultrasound energy. The controller, which may be designed as part of the power supply, will typically include a control panel and display monitor, one or more switches for current control, an input mechanism such as a keyboard, and/or a microprocessor including memory, storage and data processing capabilities for performing various functions. The controller is capable of selectively activating the switches for the transducer elements to "fire" or effect actuation of all or selected ones of the plurality of transducer elements to emit ultrasound energy. For example, switches on the controller 16 and/or the controller keyboard can be used to selectively couple and decouple the individual transducer elements 28 with the electrical drive signal or current from the power supply 14.

Input to the controller 16 provided by the surgeon or other medical personnel determines the transducer elements 28 to be actuated. For example, data entered via the controller keyboard is used to identify the particular transducer elements to be actuated, the transducer elements being identified, for example, by their location or position in the array as explained above. In this manner, the switches of selected transducer elements can be activated to permit transmission of electrical current from the power supply to the piezoelectric elements of the selected transducer elements while the switches of other selected transducer elements can remain deactivated to prevent transmission of electrical current thereto when the power supply is actuated or switched to an "on" mode. It should be appreciated that various components and/or methodology can be incorporated in the device 12, the power supply 14 and/or the controller 16 to permit selective actuation of selected ones of the transducer elements 28 and that such components and/or methodology would be within the purview of one skilled in the art.

Various transducers can be used in the focused ultrasound ablation devices of the present invention. The transducer can include an annular array, a linear array and/or a curved linear array of individual transducer elements. More than one transducer can be provided in a single ultrasound emitting member. The piezoelectric elements can be made of various piezoelectric materials such as PZT crystal materials, hard lead, zirconate/lead titanium piezoelectric ceramic, or lithium-niobate piezoceramic material. The array of piezoelectric elements can be of various sizes and patterns or configurations so that an individual array can be used to obtain lesions of various sizes and various patterns or configurations. The frequency ranges of the transducer and/ or the individual transducer elements can vary depending on clinical needs. Preferably, the transducer frequency will allow thermal ablation of anatomical tissue to be effected at the target area in response to the application or delivery of ultrasound energy to the tissue for a relatively short duration or length of time.

It should be appreciated that the focused ultrasound ablation device 12 can be provided with imaging capabilities for visualizing operative sites at which the focused ultrasound ablation device is to be used, for visualizing guidance and/or positioning of the ultrasound emitting member at the operative sites and/or for examination and diagnosis. The focused ultrasound ablation device 12 can thusly be used for both therapy and imaging, and observation of a detected image can be obtained at locations remote from the operative sites. For example, the ultrasound emitting member 18 can be provided with an ultrasound imaging transducer as described in the applications incorporated herein by reference. Conventional optical guidance mechanisms, such as fiber optic mechanisms, can be used with the focused ultrasound ablation device 12 to provide remote visualization, and such optical guidance mechanisms can be separate from or formed as part of the focused ultrasound ablation device. The focused ultrasound ablation device can be provided with a viewing device such as an eyepiece on the handle shaft or the handle or a video monitor for viewing images of the operative sites from the remote locations, typically externally of the patients' bodies.

The focused ultrasound ablation device 12 of the present invention is used to ablate a target area within a larger mass, body or area of tissue to create an ablative lesion. Depending on the characteristics of the lesion, such as the dimensions of the lesion, the severity of tissue damage and/or the nature of the ablated tissue, all or part of the lesion may be naturally degraded and absorbed by the patient's body or may remain as altered tissue, such as scar tissue that is more stiff or firm than the untreated tissue. Accordingly, the lesion may be entirely absorbed, may remain entirely as altered tissue, or may be partly absorbed and partly remaining as altered tissue. Where the lesion is partly or entirely absorbed, the tissue shrinks or decreases in size. In this manner, the size or volume of the mass, body or area of tissue can be reduced and/or the configuration of the mass, body or area of tissue can be changed for various therapeutic purposes. Where the lesion remains partly or entirely as scar tissue, the scar tissue, being stiffer, firmer or more rigid than normal, undamaged tissue, is more resistant to vibration or resonance as is desirable for the treatment of various medical conditions. In addition, the scar tissue may contract, thusly reducing the size of the mass, body or area of tissue. It should be appreciated that regardless of whether the lesion is absorbed and eliminated or remains as altered tissue, partly or entirely, the mass, body or area of tissue is nonetheless "reduced". Accordingly, as used herein, "reduction" of tissue involves elimination or reduction of normal tissue by absorption of ablated tissue and/or by transformation of normal undamaged tissue into altered tissue.

In a tissue reduction or thermal ablation procedure utilizing focused ultrasound ablation device 12, the controller 16 is instructed or programmed to effect actuation or "firing" of all or less than all of the transducer elements 28 in accordance with the size and/or pattern of a lesion desired to be formed in tissue of a particular patient. In the procedure illustrated in FIG. 2, all of the transducer elements 28 are actuated or "fired"; and, accordingly, input to the controller 16 made by the surgeon or other medical personnel designates all of the transducer elements 28 to be activated by the power supply 14. The active face 32 is positioned externally adjacent or in contact with the external tissue surface 36 of tissue A of the patient at a location or operative site on tissue A aligned with a desired site or target area in the tissue for creation of a lesion as shown in FIG. 2.

Once the active face is positioned adjacent or in contact with the tissue A at the desired location, the power supply is activated or switched to an "on" mode to transmit electrical energy to the previously selected transducer elements. Since all of the transducer elements 28 have been designated or selected for actuation, electrical energy is transmitted from the power supply to each piezoelectric element. In response thereto, the piezoelectric elements vibrate and produce ultrasound energy which is focused within the tissue A at the corresponding focusing zones F. Accordingly, anatomical tissue A at the target area 34 is heated to an ablative temperature causing the subsurface or internal ablative lesion 38 to be formed in the tissue A at the target area while the ultrasound emitting member 18 remains external of and does not physically penetrate the tissue A. In addition, tissue surrounding the target area 34 is not heated to damaging levels and is thusly preserved. The lesion 38 has a length, width and depth of known parameters depending on the locations of the selected transducer elements, the intensity of the ultrasound energy, the length of the focusing zones, the temperature to which the tissue is heated and the duration of ultrasound energy delivery or application to the tissue. The lesion can have various continuous or discontinuous surface configurations, including rectangular, square and circular configurations depending on the surface configuration of the array and/or the pattern presented by the transducer elements selected for actuation. Since the transducer elements 28 are arranged in a rectangular array, the lesion 38 is continuous or solid along a rectangular surface configuration, as shown in FIG. 3, when all the transducer elements 28 are actuated.

Due to the predetermined distance D and the known length of the focusing zones, the lesion 38 begins at a beginning or starting margin 64 located a predetermined or known depth beneath or below the external tissue surface 36 and ends at an ending margin 66 located a predetermined or known depth beneath the external tissue surface 36, the distance between the beginning and ending margins corresponding to the depth of the lesion. By selecting the appropriate focusing zone depth, a desired thickness or depth of tissue between the beginning margin 64 and the external tissue surface 36 is disposed outside the target area and is therefore undamaged and preserved. By selecting the appropriate focusing zone length, the depth of the ending margin 66 within the tissue is controlled thusly ensuring that the lesion does not extend deeper than desired. Although the length and width or other external dimensions of the lesion can be determined by the locations of the "fired" transducer elements, it should be appreciated that the external dimensions of the lesion can alternatively be obtained by manually moving the member 18 from site to site on the tissue as described in the patent applications incorporated herein by reference.

The emission of ultrasound energy by ultrasound emitting member 18 is terminated by the surgeon or other operator once a desired lesion size or amount of tissue ablation has been obtained, and the member 18 is removed from the tissue A. Confirmation of lesion size can be obtained via ultrasound imaging of the tissue. In order to terminate the emission of ultrasound energy by the ultrasound emitting member, the power supply is deactivated or switched to an "off" mode so that electrical current is no longer supplied to the selected piezoelectric elements. Where one or more additional lesions are to be formed in tissue A or other tissue of the patient, the member 18 is repositioned on the tissue A or is positioned on the other tissue at another selected location or operative site, and the procedure is repeated.

The lesion 38, which contains thermally damaged or necrotized tissue, may be naturally degraded and absorbed, partially or entirely, by the patient's body such that the remaining tissue will be smaller in bulk, size or volume than it was prior to treatment. The lesion 38 may remain, partly or entirely, as altered tissue, such as relatively stiffer or firmer scar tissue, such that a lesser amount of relatively softer, normal tissue remains, whereby the tissue is of increased resistance to vibration or resonance.

FIG. 4 illustrates the ultrasound emitting member 18 when the transducer elements 28 in the outermost rows and columns of the array are not activated to emit ultrasound energy, the activated transducer elements 28 being shaded in FIG. 4. In particular, the transducer elements 28 of columns one and six and rows one and five are not actuated while the remaining transducer elements are actuated or "fired" to emit ultrasound energy when driven by the power supply as selected and controlled via the controller as described above. The activated transducer elements 28 form a rectangular pattern or sub-array forming a lesion 138 in tissue A as shown in FIG. 5. The lesion 138 is similar to the lesion 38 except that the lesion 138 is continuous or solid along a rectangular surface configuration smaller than the rectangular surface configuration for lesion 38.

Figures 6, 7:
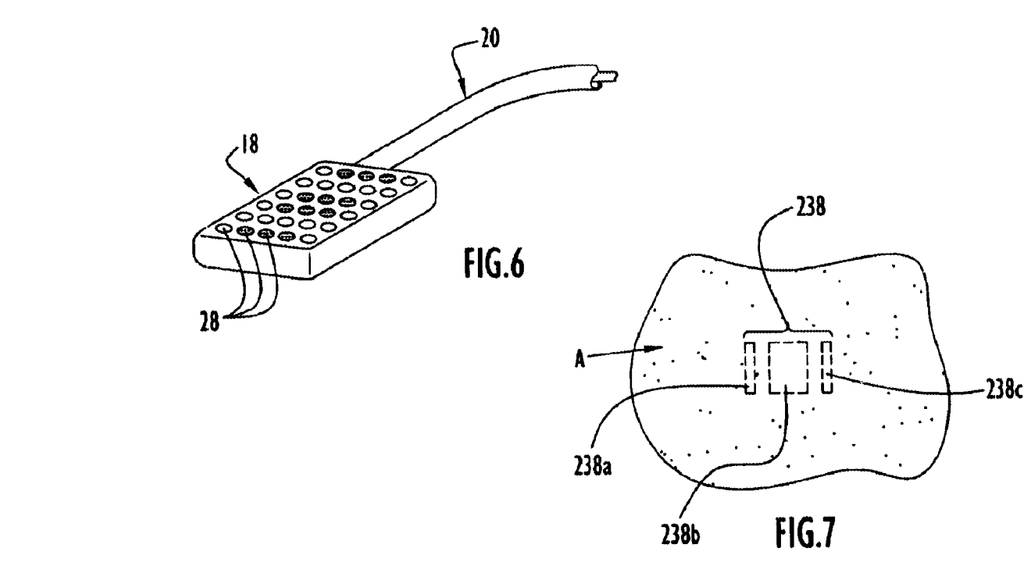
FIG. 6 is a broken perspective view of the ultrasound emitting member illustrating actuation of selected alternative ones of the plurality of ultrasound emitting elements, such selected alternative ones of the plurality of ultrasound emitting elements consisting of less than all of the ultrasound emitting elements.
FIG. 7 is a broken top view illustrating the surface configuration of a lesion formed in tissue with the focused ultrasound emitting member when actuated as depicted in FIG. 6.

FIG. 6 is illustrative of a discontinuous "firing" pattern for the array of transducer elements 28. FIG. 6 shows the ultrasound emitting member 18 With selected transducer elements 28 activated to emit ultrasound energy, the activated transducer elements 28 being shaded. In FIG. 6, the transducer elements 28 at locations R2C1, R3C1, R4C1, R2C3, R3C3, R4C3, R2C4, R3C4, R4C4, R2C6, R3C6 and R4C6 are actuated to emit ultrasound energy while the remaining transducer elements 28 are decoupled from the power supplying. The transducer elements R2C1, R3C1 and R4C1 are spaced from the transducer elements R2C3, R3C3 and R4C3, respectively. Similarly, the transducer elements R2C6, R3C6 and R4C6 are spaced from transducer elements R2C4, R3C4 and R4C4. FIG. 7 illustrates an internal lesion 238 obtained with ultrasound emitting member 18 when the transducer elements 28 are "fired" in the pattern shown in FIG. 6. As shown in FIG. 7, a discontinuous lesion 238 is formed in tissue A, the lesion 238 comprising separate, disconnected lesion segments 238a, 238b and 238c. Lesion segment 238b is centrally located between lesion segments 238a and 238c and has a length and width corresponding or substantially corresponding to the length and width of a rectangular sub-array formed by the transducer elements 28 at locations R2C3, R2C4, R3C3, R3C4, R4C3 and R4C4. Accordingly, lesion segment 238b is continuous or solid along a surface area of rectangular configuration. Lesion segments 238a and 238c are similar to one another and are disposed on opposite sides of lesion segment 238b. Lesion segments 238a and 238c are spaced from lesion segment 238b, and the tissue segments between lesion segment 238b and lesion segments 238a and 238c, respectively, are undamaged and preserved. Lesion segment 238a has a length and width corresponding or substantially corresponding to the length and width of a sub-array formed by the transducer elements 28 at locations R2C1, R3C1 and R4C1. Lesion segment 238c has a length and width corresponding or substantially corresponding to the length and width of a sub-array formed by transducer elements 28 at locations R2C6, R3C6 and R4C6. The lesion segments 238a and 238c are each solid or continuous along a surface area of rectangular configuration, the lesion segments 238a and 238c having the same length as lesion segment 238b but having a width smaller or less than the width of lesion segment 238b. The lesion 238 may be considered an ablated tissue area containing unablated tissue, i.e. the tissue between the lesion segments, and a plurality of lesions, i.e. the lesion segments, at which the tissue is ablated. Of course, the location of the lesions, i.e. the lesion segments, corresponds to the focusing zones of the actuated transducer elements.

Figure 8:
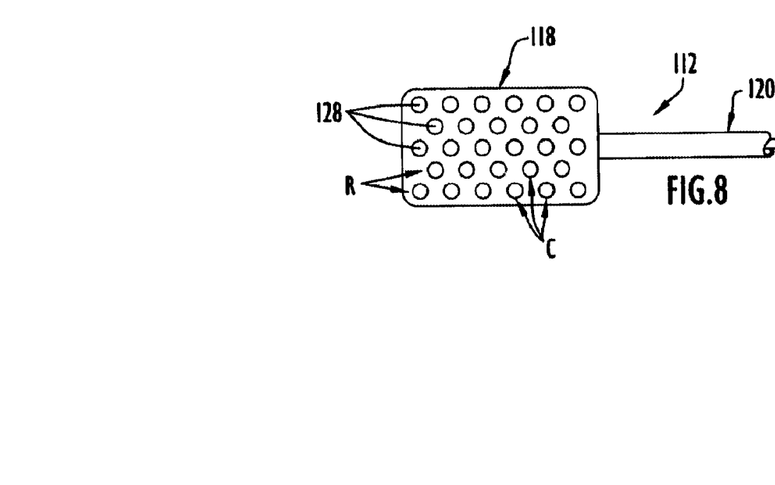
FIG. 8 is a broken perspective view illustrating an alternative focused ultrasound ablation device according to the present invention.

An alternative focused ultrasound ablation device according to the present invention is illustrated at 112 in FIG. 8. Focused ultrasound ablation device 112 includes ultrasound emitting member 118 carried by handle 120 and is similar to focused ultrasound ablation device 12 except that the transducer elements 128 of the focused ultrasound emitting member 118 are arranged in rows R that are staggered or offset from one another. In particular, the array formed by transducer elements 128 has a generally rectangular configuration with five rows of transducer elements 128, the transducer elements of rows two and four being offset from or not aligned with the transducer elements of rows one, three and five. In addition, the rows R do not contain an equal number of transducer elements 128. Rows one, three and five contain six transducer elements and rows two and four contain five transducer elements. Also, since the rows R are staggered, the array includes eleven columns C. Columns one, three, five, seven, nine and eleven each contain three transducer elements while columns two, four, six, eight and ten each contain two transducer elements. As described for focused ultrasound emitting member 18, all or selected ones of the transducer elements 128 can be actuated or "fired" to emit ultrasound energy.

With the present invention, a single focused ultrasound ablation device can be used to form lesions of various sizes and/or surface configurations or patterns in anatomical tissue via actuation of selected transducer elements of the focused ultrasound emitting member. In this manner, lesion size and/or surface configuration can be optimally selected for individual patients. The lesions formed in accordance with the present invention can have continuous or solid surface configurations, or the lesions can be comprised of disconnected surface configuration segments. Where lesions comprised of disconnected surface configuration segments are formed in anatomical tissue, thermal damage to the tissue disposed between, around or surrounding the individual surface configuration segments can be avoided. Since various sizes and/or configurations or patterns of lesions can be obtained with a singled focused ultrasound ablation device, a single focused ultrasound ablation device can be used to ablate various types of anatomical tissue or structures at various operative sites within or on patients' bodies. The high intensity focused ultrasound ablation device of the present invention can thusly be provided as a standardized device capable of being used in diverse thermal ablation or tissue reduction procedures. Lesions formed with the ablation devices according to the present invention can be disposed below the external tissue surface or can include the external tissue surface as described in the application incorporated herein by reference and entitled Methods of Tonsil Reduction By Thermal Ablation Using High Intensity Focused Ultrasound. The focused ultrasound ablation devices of the present invention can be used in various anatomical areas including the soft palate, tongue, tonsils, turbinates or other soft tissue of the head or neck, and skin as disclosed in the patent applications incorporated herein by reference as well as various other anatomical areas.

Inasmuch as the present invention is subject to many variations, modifications and changes in detail, it is intended that all subject matter discussed above or shown in the accompanying drawings be interpreted as illustrative only and not be taken in a limiting sense.

What is claimed is:

1. A focused ultrasound ablation device for creating a lesion in anatomical tissue of a patient comprising
   an ultrasound emitting member including an active surface adapted for positioning adjacent anatomical tissue, said active surface carrying a plurality of individual ultrasound emitting elements arranged in an array along said active surface, said ultrasound emitting elements being actuatable to emit ultrasound energy and focus the emitted ultrasound energy at focusing zones, each focusing zone being separate and distinct to the ultrasound emitting element, and each focusing zone being spaced from one another and located the same fixed predetermined distance outwardly from said active surface whereby the ultrasound energy is focused within the anatomical tissue to form a lesion within the tissue, said ultrasound emitting elements in said array being selectively, independently actuatable to emit ultrasound energy therefrom and being selectively, independently non-actuatable to not emit ultrasound energy therefrom in response to selection by an operator of a particular size and surface configuration for the lesion to be formed within the tissue in accordance with the positions in said array of said ultrasound emitting elements selected to be actuated; and
   a handle coupled to said ultrasound emitting member 2. A focused ultrasound ablation device as recited in claim 1 wherein said ultrasound emitting elements are arranged along said active surface in rows and columns forming said array.

3. A focused ultrasound ablation device as recited in claim 2 wherein said ultrasound emitting elements each include a piezoelectric element that emits ultrasound energy in response to electric current selectively supplied thereto.

4. A focused ultrasound ablation device as recited in claim 3 wherein said piezoelectric elements are curved to effect focusing of the ultrasound energy said predetermined distance from said active surface.

5. A focused ultrasound ablation device as recited in claim 2 wherein said ultrasound emitting elements of said rows are vertically aligned with one another.

6. A focused ultrasound ablation device as recited in claim 2 wherein said ultrasound emitting elements of said rows are vertically offset from one another.

7. A focused ultrasound ablation device for creating a lesion in anatomical tissue of a patient comprising
   an ultrasound emitting member comprising an active face adapted for positioning adjacent anatomical tissue, said active face carrying a planar array of ultrasound transducer elements, said ultrasound transducer elements each emitting ultrasound energy in response to an electrical signal supplied thereto, said ultrasound transducer elements having focusing configurations, respectively, by which ultrasound energy emitted therefrom is focused at focusing zones, respectively, located the same fixed predetermined distance from said active face such that the anatomical tissue is heated at the focusing zones, respectively, to form a lesion within the anatomical tissue, said ultrasound transducer elements in said array being selectively, independently actuatable to emit ultrasound energy and being selectively, independently non-actuatable to not emit ultrasound energy in response to selection by an operator of a particular size and surface configuration for the lesion to be formed within the tissue; and
   a handle coupled to said ultrasound emitting member.

8. A focused ultrasound ablation device as recited in claim 7 wherein said transducer elements are spaced from one another in said planar array.

9. A focused ultrasound ablation device as recited in claim 8 wherein said active face is adapted to be placed against an external surface of the tissue whereby said focusing zones are disposed in the tissue said predetermined distance from the external surface.

10. A focused ultrasound ablation device as recited in claim 8 wherein said transducer elements are arranged in a plurality of rows and columns forming said array.

11. A focused ultrasound ablation device as recited in claim 10 wherein each of said transducer elements includes a piezoelectric element.

12. A focused ultrasound ablation device as incited in claim 7 and further including an elongate handle shaft by which said handle is coupled to said ultrasound emitting member, said handle shaft having a distal end coupled to said ultrasound emitting member and having a proximal end coupled to said handle.

13. A method of thermal ablation of anatomical tissue using focused ultrasound comprising the steps of
- selecting one or more of a plurality of individual ultrasound emitting elements, arranged in an array on an active face of an ultrasound emitting member, for actuation to emit ultrasound energy in accordance with a desired size and surface configuration of a lesion to be formed in anatomical tissue;
- positioning the active face adjacent the anatomical tissue at a location aligned with a desired target area for the lesion within the tissue;
- actuating the selected one or more ultrasound emitting elements to emit ultrasound energy;
- focusing the ultrasound energy with the selected one or more of the ultrasound emitting elements so that the ultrasound energy is focused in the target area at one or more focusing zones corresponding to the selected one or more of the ultrasound emitting elements, each of the one or more focusing zones being disposed the same fixed predetermined distance from the active face; and
- heating the tissue with the focused ultrasound energy to form a lesion at the target area having the desired size and surface configuration.

14. The method of thermal ablation as recited in claim 13 wherein the ultrasound emitting elements emit ultrasound energy in response to an electrical signal supplied thereto and said step of actuating includes electrically coupling the selected one or more of the ultrasound emitting elements with an electrical signal source.

15. The method of thermal ablation recited in claim 14 wherein said step of electrically coupling includes electrically coupling the selected one or more of the ultrasound emitting elements with a power supply producing the electrical signal.

16. The method of thermal ablation recited in claim 13 wherein said step of positioning includes positioning the active face of the ultrasound emitting member against an external surface of the tissue.

17. The method of thermal ablation recited in claim 16 wherein said step of focusing includes focusing the ultrasound energy so that each focusing zone is disposed a predetermined depth beneath the external surface of the tissue.

18. The method of thermal ablation recited in claim 13 wherein said step of selecting includes selecting a plurality of the plurality of ultrasound emitting elements to form a lesion of continuous planar surface area within the tissue.

19. The method of thermal ablation recited in claim 13 wherein said step of selecting includes selecting a plurality of the plurality of ultrasound emitting elements to form a lesion of discontinuous planar surface area in the tissue.

20. The method of thermal ablation recited in claim 19 wherein said step of selecting includes selecting a plurality of the plurality of ultrasound emitting elements to form a lesion comprising a plurality of planar, disconnected lesion segments in the tissue.

21. The method of thermal ablation recited in claim 20 wherein said step of selecting includes selecting a plurality of the plurality of ultrasound emitting elements to form a plurality of planar, disconnected lesion segments each surrounded by thermally undamaged portions of the tissue.

22. The method of thermal ablation as recited in claim 13 and further including, subsequent to said step of heating, the step of allowing at least part of the lesion to be naturally absorbed by the patients body.

23. The method of thermal ablation as recited in claim 13 and further including, subsequent to said step of heating, the step of allowing at least part of the lesion to remain as scar tissue in the patient's body.

24. A method of thermal ablation of anatomical tissue comprising the steps of
- positioning an active surface of an ultrasound emitting member adjacent anatomical tissue to be ablated;
- actuating a plurality of ultrasound emitting elements disposed along the active surface to emit ultrasound energy;
- emitting ultrasound energy into the anatomical tissue from the plurality of ultrasound emitting elements disposed along the active surface;
- focusing the ultrasound energy at a plurality of focusing zones contained in a target area in the anatomical tissue, each focusing zone being separate and distinct to the ultrasound emitting element and each focusing zone being disposed the same predetermined distance from the ultrasound emitting elements;
- heating the anatomical tissue at the focusing zones with the focused ultrasound energy to form an ablated tissue area at the target area containing a plurality of lesions at the focusing zones, respectively; and
- removing the active surface from adjacent the anatomical tissue.

25. The method of thermal ablation of anatomical tissue as recited in claim 24 wherein said step of positioning includes positioning the active surface adjacent an external surface of the anatomical tissue and said step of focusing includes focusing the ultrasound energy in a target area disposed beneath the external surface.

26. The method of thermal ablation of anatomical tissue as recited in claim 25 wherein said step of positioning includes positioning the active surface in contact with the external surface.

27. The method of thermal ablation of anatomical tissue as recited in claim 25 wherein said step of heating includes heating the anatomical tissue at the focusing zones with the focused ultrasound energy so that the lesions begin at a beginning margin located below the external surface and end at an ending margin located further below the external surface than the beginning margin.

28. The method of thermal ablation of anatomical tissue as recited in claim 24 wherein said step of heating includes forming the ablated tissue area surrounded by unablated anatomical tissue.

29. The method of thermal ablation of anatomical tissue as recited in claim 28 wherein said step of heating includes forming the ablated tissue area so that the plurality of lesions do not contact one another.

30. A method of thermal ablation of anatomical tissue comprising the steps of
- positioning an active surface of an ultrasound emitting member adjacent anatomical tissue to be ablated;
- actuating a plurality of ultrasound emitting elements disposed in a plane along the active surface to emit ultrasound energy;
- emitting ultrasound energy from the plurality of ultrasound emitting elements disposed in the plane along the active surface;
- focusing the ultrasound energy in the anatomical tissue at a plurality of closely spaced focusing zones corresponding to the ultrasound emitting elements, each focusing zone is being separate and distinct to the ultrasound emitting elements, and each focusing zone being disposed in a plane located a fixed predetermined distance from the active surface;

ablating the anatomical tissue with the focused ultrasound energy to form an ablated tissue area containing a plurality of lesions at the focusing zones, respectively; and removing the ultrasound emitting member from adjacent the anatomical tissue.

31. The method of thermal ablation of anatomical tissue as recited in claim 30 wherein said step of positioning includes positioning the active surface adjacent an external surface of the anatomical tissue.

32. The method of thermal ablation of anatomical tissue as recited in claim 31 wherein said step of positioning includes positioning the active surface in contact with the external surface.

33. The method of thermal ablation of anatomical tissue as recited in claim 30 wherein said step of ablating includes forming a planar ablated tissue area.

34. The method of thermal ablation of anatomical tissue as recited in claim 33 wherein said step of ablating includes forming the plurality of lesions to begin at a beginning margin located below the external surface and to end at an ending margin located further below the external surface than the beginning margin.

35. A method of thermal ablation of anatomical tissue comprising the steps of positioning an active surface of an ultrasound emitting member adjacent anatomical tissue and in alignment with a target area in the anatomical tissue at which an ablated tissue area is to be created;

actuating selected ones of a plurality of ultrasound emitting elements disposed along the active surface to emit ultrasound energy;

emitting ultrasound energy from the selected ultrasound emitting elements into the anatomical tissue;

focusing the ultrasound energy in the anatomical tissue at a plurality of focusing zones corresponding to the selected ultrasound emitting elements, each focusing zone being separate and distinct to the ultrasound of emitting element, and each focusing zone being disposed the same predetermined distance from the ultrasound emitting elements; and ablating the anatomical tissue with the focused ultrasound energy to form an ablated tissue area at the target area having a planar surface configuration containing a plurality of closely spaced lesions at which the anatomical tissue is ablated.

36. The method of thermal ablation of anatomical tissue as recited in claim 35 and further including, prior to said step of actuating, the step of selecting the ultrasound emitting elements to be actuated.

37. The method of thermal ablation of anatomical tissue as recited in claim 35 wherein said step of focusing includes focusing the ultrasound energy at a plurality of closely spaced focusing zones disposed below an external surface of the anatomical tissue.

38. A focused ultrasound ablation device for creating an ablated tissue area in anatomical tissue comprising an ultrasound emitting member including an active surface adapted for positioning adjacent anatomical tissue and a plurality of individual ultrasound emitting elements arranged in a plane along said active surface, said ultrasound emitting elements being actuatable to emit ultrasound energy and focus the emitted ultrasound energy at a plurality of focusing zones, each focusing zone being separate and distinct to the ultrasound emitting element, and each focusing zone being disposed in a plane located a predetermined distance outwardly from said plane of said ultrasound emitting elements whereby the ultrasound energy is focused within the anatomical tissue to form a lesion within the anatomical tissue, said ultrasound emitting elements disposed along said active surface being selectively, independently actuatable to emit ultrasound energy and being selectively, independently non-actuatable to not emit ultrasound energy in response to selection by an operator of a particular size and surface configuration for the lesion; and a handle coupled to said ultrasound emitting member.

39. A focused ultrasound ablation device as recited in claim 38 wherein said ultrasound emitting elements are fixed in a planar array along said active surface.

40. A focused ultrasound ablation device for creating an ablated tissue area in anatomical tissue comprising an ultrasound emitting member comprising an active face adapted for positioning adjacent anatomical tissue and carrying a plurality of spaced ultrasound emitting elements fixed in a planar array along said active face and capable of emitting ultrasound energy, said ultrasound emitting elements being selectively actuatable to focus the ultrasound energy emitted therefrom at a plurality of spaced focusing zones, each focusing zone being separate and distinct to the ultrasound emitting element, and each focusing zone being disposed in a plane located a fixed predetermined distance from said active face such that the anatomical tissue is heated at the focusing zones, respectively, to forms planar ablated tissue area in the anatomical tissue containing a plurality of lesions at the focusing zones, respectively, at which the anatomical tissue is ablated; and a handle coupled to said ultrasound emitting member.

41. A focused ultrasound ablation device as recited in claim 40 wherein said ultrasound emitting elements are selectively actuatable to emit ultrasound energy.

42. A focused ultrasound ablation device as recited in claim 40 wherein each of said ultrasound emitting elements includes a piezoelectric element.

* * * * *